US007635396B2

(12) United States Patent
Reuter et al.

(10) Patent No.: US 7,635,396 B2
(45) Date of Patent: Dec. 22, 2009

(54) PROCESS FOR SEPARATING ZIRCONIUM AND HAFNIUM

(75) Inventors: Knud Reuter, Krefeld (DE); Gerd Passing, Hürth (DE); Stephan Kirchmeyer, Leverkusen (DE)

(73) Assignee: H.C. Starck GmbH (DE)

( * ) Notice: Subject to any disclaimer, the term of this patent is extended or adjusted under 35 U.S.C. 154(b) by 274 days.

(21) Appl. No.: 11/743,175

(22) Filed: May 2, 2007

(65) Prior Publication Data

US 2007/0283536 A1 Dec. 13, 2007

(51) Int. Cl.
*C22B 34/14* (2006.01)
*C07F 7/00* (2006.01)

(52) U.S. Cl. ........................................ 23/305 R; 556/52

(58) Field of Classification Search ................... 556/52; 23/305 R

See application file for complete search history.

(56) References Cited

U.S. PATENT DOCUMENTS

| 5,188,916 | A | 2/1993 | Hodumi et al. | |
|---|---|---|---|---|
| 7,196,211 | B2 * | 3/2007 | Itsuki et al. | 556/51 |
| 2006/0062910 | A1 | 3/2006 | Meiere | |

FOREIGN PATENT DOCUMENTS

| AT | 108778 | 7/1983 |
|---|---|---|
| CH | 639127 | 10/1983 |

OTHER PUBLICATIONS

McCoy. M., "Forging the way to high-k dielectrics", C & EN, 2005, pp. 26-29.

Pickles, C. A., et al., "Separation of HfCl$_4$ from ZrCl$_4$ by reaction with solid and liquid alkali chlorides under non-equilibrium conditions", Canadian Metallurgical Quarterly, 1997, vol. 36, No. 2, pp. 131-136.

Fischer, WF., et al., "Grundlagen und entwicklung des verfahrens zur trennung der elemente zirkonium und hafnium durch verteilen ihrer thiocyanate", Angew. Chem., 1966, vol. 78, No. 1, pp. 19-27, p. 2, Lines 23-25 of the Spec.

da Silva, A.B.V., et al., "Zirconium and hafnium separation without waste generation", CIM Bulletin, 1998, vol. 91, pp. 221-224.

Da Silva, A., et al., "Hafnium/zirconium separation using cyanex 925", Canadian Metallurigical Quarterly, 2000, vol. 39, No. 1, pp. 37-42.

Yang, X. J., et al., "Separation of hafnium from zirconium by extraction chromatography with liquid anionic exchangers", Journal of Chromatographic Science, 1999, vol. 37, pp. 171-179.

Yang, X. J. et al., "Separation of zirconium and hafnium using hollow fibers part I. supported liquid membranes", Chemical Engineering Journal, 2002, vol. 88, pp. 37-44.

Yang, X. J., et al,, "Separation of zirconium and hafnium using hollow fibres part II, membrane chromatography", Chemical Engineering Journal, 2002, vol. 88, pp. 45-51.

Wende, H. C., et al., "Atomspektrometrie in der industriellen praxis", Nacgrichten aus der Chemie, 2004, vol. 52, pp. 1152-1154, p. 7, Lines 23-25, and p. 8, Lines 19-20-25 of the Spec of the Spec.

Nölte, J., et al., "ICP-OES: Entwicklungen in den letzten 25 jahren", CLB Chemie in Labor und Biotechnik, 2000, vol. 51, pp. 286-292, p. 8, Lines 20-21 of the Spec.

* cited by examiner

*Primary Examiner*—Porfirio Nazario Gonzalez
(74) *Attorney, Agent, or Firm*—Connolly Bove Lodge & Hutz LLP

(57) ABSTRACT

The present invention provides a new process for separating zirconium and hafnium compounds, in particular to remove traces of zirconium compounds from hafnium compounds, using fractional crystallisation, as well as hafnium compounds obtainable in accordance with this process.

17 Claims, No Drawings

PROCESS FOR SEPARATING ZIRCONIUM AND HAFNIUM

RELATED APPLICATIONS

This application claims benefit of German application 10 2006 020 440.9 filed May 3, 2006.

The present invention provides a new process for separating zirconium and hafnium compounds, in particular to remove traces of zirconium compounds from hafnium compounds, using fractional crystallisation, as well as hafnium compounds obtainable in accordance with this process.

Hafnium occurs naturally, but always along with zirconium, e.g. in the minerals zirconia and baddeleyite, in relatively small proportions of about 2 to 7 wt. %. Zirconium and hafnium, as a result of their extreme chemical similarity, inter alia due to the so-called lanthanide contraction, are among the most difficult elements in the periodic system of elements to separate.

Technically, the separation of zirconium and hafnium is important due to the very different neutron capture cross-sections of their atomic nuclei, this being important for use of the metals in nuclear power stations. Since the main use of zirconium, with its very low neutron absorption, is as a cladding material in reactor engineering, it is especially important to produce zirconium that contains as little hafnium as possible. In addition, in the industrial processes for producing zirconium, hafnium is ultimately produced as an inevitable final product, wherein the purity, i.e. the absence of zirconium, is of little relevance. Technical grade hafnium and its compounds, e.g. hafnium oxide or hafnium chloride, are therefore depleted in zirconium, but often only to zirconium contents of about 2 wt. %. Typical commercially available hafnium compounds therefore contain 1000-2000 ppm by wt., or more, zirconium in the form of the analogous zirconium compounds; see also e.g. Chem & Eng. News 83(26), 2005, p. 26-29. When hafnium is used as a moderator in nuclear engineering, this being based on its high capture cross-section for neutrons, zirconium impurities in amounts of this order of magnitude play a subordinate role.

In the microelectronics field, hafnium compounds are playing an increasing part as precursor compounds (so-called precursors) in Chemical Vapour Deposition (CVD or MOCVD=Metal Organic CVD) and in the special embodiment of this called ALD (Atomic Layer Deposition). From such volatile, readily vaporisable precursors, functional layers of nitrides, such as HfN as a barrier layer or contact layer, or oxides ($HfO_2$), optionally also mixed oxides or oxynitrides with other elements such as Al, Si etc, as dielectrics with particularly high dielectric constants, are deposited on a substrate such as e.g. a silicon wafer, using CVD technology. In order to make full use of the advantageous properties of the functional layers of inorganic hafnium compounds, it is desirable to keep the zirconium content as low as possible; see also Chem & Eng. News 83(26), 2005, p. 26-29.

The current techniques for separating hafnium and zirconium are associated with various disadvantages, wherein in particular the depletion of zirconium to values of lower than 500 ppm by wt., or further to 100 ppm by wt., is a serious problem.

Low-zirconium hafnium chloride can be prepared, for example, by distillation of the molten salt, but purification down to very low zirconium contents is extraordinarily costly. Another route to deplete the zirconium goes via hafnium oxide and that then has to be rechlorinated (by carbochlorination), a costly process. Other processes, for example solvent extraction from HCl solutions of the thiocyanate complexes with methyl-isobutyl ketone or specific trialkylphosphane oxides are, inter alia, associated with effluent problems (cyanide!) or are not advantageous due to the poor, in some circumstances non-existent, industrial availability of the phosphorus compounds (trialkylphosphane oxides). See e.g. C. A. Pickles and S. N. Flengas, Canadian Metallurgical Quarterly 36(2), 1997, p. 131-136; W. F. Fischer, B. Deierling, H. Heitsch, G. Otto, H.-P. Pohlmann and K. Reinhardt, Angew. Chem. 78(1), 1966, p. 19-27; A. B. V. da Silva and P. A. Distin, CIM Bulletin 91(1018), 1998, p. 221-224; A. da Silva, E. El-Ammouri and P. A. Distin, Canadian Metallurgical Quarterly 39(1), 2000, p. 37-42; X. J. Xang, C. Pin and A. G. Fane, J. Chromatographic Sci. 37(5), 1999, p. 171-179; X. J. Xang, A. G. Fane and C. Pin, Chem. Eng. J. 88, 2002, p. 37-44; X. J. Xang, A. G. Fane and C. Pin, Chem. Eng. J. 88, 2002, p. 45-51.

Furthermore there is thus a demand for a simple and effective process for separating zirconium and hafnium compounds, in particular to produce low-zirconium hafnium compounds that do not have the disadvantages described above.

Therefore, the object of the present invention is to find such a process. Another object is to prepare hafnium compounds with a zirconium content of less than 500 ppm by wt., preferably less than 100 ppm by wt.

Surprisingly it was found that special zirconium and hafnium organic compounds, in the following simplified to zirconium and hafnium compounds, the other properties of which are very similar, can be separated from each other by simple fractional crystallisation.

Thus, the present invention provides a process for separating zirconium and hafnium compounds, characterised in that a mixture of $HfR_4$ and $ZrR_4$, in which R represents an organic group that optionally contains one or more heteroatoms and that contains at least one carbon atom, is subjected to fractional crystallisation.

The process according to the invention can be used equally either to produce purified hafnium compounds by removing impurities in the form of zirconium compounds or to produce purified zirconium compounds by removing impurities in the form of hafnium compounds. However, the production of purified hafnium compounds by removing impurities in the form of zirconium compounds is preferred. The process according to the invention is particularly suitable for separating those mixtures containing at most 3 wt. %, preferably at most 0.3 wt. % of zirconium, with respect to the total weight of the mixture. Such mixtures are obtained, for example, during the depletion of hafnium in zirconium described above and are therefore present in most technical grade hafnium compounds.

In the context of the present invention, a mixture is understood to be either a homogeneous or a heterogeneous mixture. Macroscopic and microscopic mixtures are included therein.

The fractional crystallisation is preferably performed at temperatures between −70° C. and +100° C., preferably between −20° C. and +70° C.

The fractional crystallisation in accordance with the process according to the invention is preferably a melt crystallisation. However, this may be performed in the presence of small amounts of an inert organic solvent or, preferably, in the absence of any solvent at all. Optionally, proportions of up to 10 wt. % of an inert solvent, that is to say one that does not react with the highly reactive Zr and Hf compounds, may be advantageous in the melt in order to adjust to optimum crystallisation conditions. Such solvents are, for example, aliphatic, cycloaliphatic or aromatic hydrocarbons such as pentane, hexane, heptane, cyclohexane, toluene or xylene, or aliphatic open-chain or cyclic ethers such as diethyl ether, di-n-propyl ether, di-iso-propyl ether, di-n-butyl ether, tert-butyl methyl ether, tetrahydrofuran or dioxan. However, solvent proportions of up to 3 wt. % are preferred and particularly preferably no solvent is present in the melt.

Preferred zirconium and hafnium compounds $ZrR_4$ and $HfR_4$ are those in which R represents identical or different groups $YR^1$ or $NR^2R^3$, in which Y represents O or S and $R^1$, $R^2$, $R^3$ each, independently, represent a linear or branched, optionally substituted $C_1$-$C_{18}$-alkyl group, an optionally substituted $C_3$-$C_6$-cycloalkyl group or an optionally substituted $C_5$-$C_{24}$-aryl group.

Particularly preferred zirconium and hafnium compounds $ZrR_4$ and $HfR_4$ are those in which R represents identical $C_1$-$C_6$-oxyalkyl or di($C_1$-$C_6$)-alkyl)amino groups. Di($C_1$-$C_6$)-alkyl)amino groups are very particularly preferred.

With regard to bonding or coordination of the groups R to the Hf or Zr centre, it is not critical whether the groups R are bonded directly to the central zirconium or hafnium atom via one or more carbon atom(s) or via one or more heteroatom(s) such as O, S, N, P, Si etc.

$C_1$-$C_6$-alkyl represents, for example, methyl, ethyl, n-propyl, iso-propyl, n-butyl, sec-butyl, tert-butyl, n-pentyl, 1-methylbutyl, 2-methylbutyl, 3-methylbutyl, neo-pentyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl or 1-ethyl-3-methylpropyl, $C_1$-$C_{18}$-alkyl represents, in addition to these and by way of example, n-heptyl and n-octyl, pinyl, adamantyl, the isomeric menthyls, n-nonyl, n-decyl, n-dodecyl, n-tridecyl, n-tetradecyl, n-hexadecyl, n-octadecyl or stearyl. The preceding definitions of alkyl given by way of example also apply to those groups that contain such an alkyl group, such as e.g. oxyalkyl groups.

$C_3$-$C_6$-cycloalkyl represents, for example, cyclopropyl, cyclobutyl, cyclopentyl or cyclohexyl.

Aryl represents, independently each time, an aromatic group with 5 to 24 skeleton carbon atoms in which, however, none, one, two or three skeleton carbon atoms per ring, but at least one skeleton carbon atom in the whole molecule, may be replaced by heteroatoms, chosen from the group comprising nitrogen, sulfur or oxygen, but preferably represents a carbocyclic aromatic group with 6 to 24 skeleton carbon atoms.

Examples of $C_6$-$C_{24}$-aryl groups are phenyl, o-, m-, p-toluene, naphthyl, phenanthrenyl, anthracenyl or fluorenyl, examples of heteroaromatic $C_5$-$C_{24}$-aryl groups in which none, one, two or three skeleton carbon atoms per ring, but at least one skeleton carbon atom in the whole molecule, may be substituted by heteroatoms, chosen from the group comprising nitrogen, sulfur or oxygen, are for example pyridyl, pyridyl-N-oxide, pyrimidyl, pyridazinyl, pyrazinyl, thienyl, furyl, pyrrolyl, pyrazolyl, imidazolyl, thiazolyl, oxazolyl or isoxazolyl, indolizinyl, indolyl, benzo[b]thienyl, benzo[b]furyl, indazolyl, quinolyl, isoquinolyl, naphthyridinyl, quinazolinyl, benzofuranyl or dibenzofuranyl.

A highly suitable example of hafnium and zirconium compounds to be separated is in particular the corresponding dimethylamides of Hf and Zr. The melting points of hafnium tetrakis(dimethylamide) and zirconium tetrakis(dimethylamide) differ by about 35° C., wherein the zirconium compound is the higher melting and therefore is preferentially frozen out of a melt of a mixture of the two compounds. Thus, under crystallisation conditions, the proportion of zirconium compound decreases and a purified hafnium tetrakis(dimethylamide) is obtained in the liquid phase.

The use of dialkylamides, in particular the dimethylamides, to remove traces of zirconium from the corresponding hafnium compounds is, for various reasons, a particularly preferred embodiment of the invention. On the one hand, hafnium amides are highly suitable compounds for use as CVD precursors that can be used e.g. to deposit hafnium nitride (HfN) or hafnium oxide ($HfO_2$), so the purified hafnium compounds can be used directly in the CVD process. Furthermore, these amides are suitable, due to their high reactivity towards all compounds with mobile hydrogen atoms, for preparing other, more reactive CVD precursors. For example, e.g. hafnium oxide or hafnium tert.butoxide, described as a very volatile precursor, can be obtained with alcohols or alkoxides, or corresponding cyclopentadienyl complexes are obtained with cyclopentadiene by replacing some of the amino groups. The corresponding hafnium tetrakis(dialkylamide) compounds can be obtained from hafnium tetrakis(dimethylamide) by transamidation with only slightly volatile higher homologues, e.g. methylethylamine or diethylamine, wherein dimethylamine is evolved and escapes as a gas at room temperature.

Another example of the use of the process according to the invention involves the tert.butoxides of Zr and Hf, where $Zr(O^tBu)_4$ again has the higher melting point, 3° C., so that it is preferentially frozen out of $Hf(O^tBu_4)$ melts that are kept at just below this temperature.

An essential feature for the suitability of such compounds for use in the process according to the invention is the different tendency to crystallise out of the melt, caused by sufficiently differing melting points, that leads to enrichment of one compound in the liquid phase and corresponding depletion in the solid phase. In the process according to the invention the zirconium compound preferably has a melting point that is at least 3° C., preferably at least 10° C., particularly preferably at least 20° C., higher than the hafnium compound. The zirconium compound then becomes enriched in the solid phase, whereas the purified hafnium compound remains in the liquid phase.

The process according to the invention is performed, for example, in such a way that a mixture of the zirconium and hafnium compounds is first fully melted, then the temperature is lowered to a temperature below the melting point of the higher melting compound but above that of the lower melting compound and finally the melt is held at that temperature for a period of 1 to 24 hours. This procedure may be repeated several times with the separated phases.

The process according to the invention is suitable, inter alia, for producing hafnium compounds with a zirconium content of less than 500 ppm by wt., preferably less than 100 ppm by wt., with respect to the total weight. Such hafnium compounds could not previously be obtained using traditional methods of purification.

The concentration of zirconium, or also hafnium, can be determined using a variety of methods, such as for example AAS (atomic absorption spectroscopy), ICP-OES (inductively coupled plasma optical emission spectroscopy) or ICP-MS (inductively couples plasma mass spectrometry), see e.g. M. C. Wende, M. Luebke, A. Gross, K.-P. Jaeckel, Nachrichten aus der Chemie 52(11), 2004, p. 1152-1154. These analytical methods are known to a person skilled in the art and provide values that are independent of the method of measurement.

The invention thus also provides the purified hafnium compounds that can be obtained using the process according to the invention.

The following examples are intended to illustrate the present invention but should not be regarded as restrictive.

EXAMPLES

Example 1

37 g of hafnium tetrakis(dimethylamide) with a concentration of 565 ppm by wt. of Zr were fully melted at 45° C. and then held at a temperature of 23° C. for 16 hours. The mixture then consisted of 22 g of crystalline phase and 15 g of liquid phase. According to ICP-OES analysis, the liquid phase contained only 415 ppm by wt. of zirconium, while in contrast the solids contained 660 ppm by wt. of Zr.

ICP-OES (inductively coupled plasma optical emission spectroscopy) analysis and the method of performing this is known to a person skilled in the art and is described, for example in M. C. Wende, M. Luebke, A. Gross, K.-P. Jaeckel, Nachrichten aus der Chemie 52(11), 2004, p. 1152-1154 and J. Nolte, CLB Chemie in Labor und Biotechnik 51(8), 2000, p. 286-292.

Example 2

164.7 g of hafnium tetrakis(dimethylamide) with a 0.81 wt.-% Zr content were treated analogously to Example 1. The procedure was repeated with the liquid phase first obtained (1) twice more, obtaining phases (2) and (3). The liquid phases contained the following amounts of Zr (measured by ICP-OES):

(1) 0.77 wt.-%

(2) 0.69 wt.-%

(3) 0.59 wt.-%, demonstrating the increasing purification effect (decreasing Zr content). The yields of purified liquid phase were: step (1) 72%, step (2) 80%, and step (3) 57%, relative to the total amide amount before separation of the liquid phase in each step.

Example 3

Here the accumulating effect of Zr in the crystalline, removed parts is demonstrated. From 95 g of hafnium tetrakis (dimethylamide) with 0.72 wt.-% Zr content step by step 26.9 g, 19.5 g and 26.0 g of liquid phase were removed by repeated partial melting at ca. 30° C. and crystallising again at 0°. The crystalline phase remaining at last (21.8 g) contained 1.3 wt.-% Zr.

The combined liquid phases were treated twice in the same manner as in example 2, removing the higher melting, more Zr-contaminated solid part. The liquid phase remaining at last at ca. 23° C. (19.4 g) contained 0.57 wt % Zr.

The invention claimed is:

1. A process for separating zirconium and hafnium compounds which comprises subjecting a mixture of $HfR_4$ and $ZrR_4$ to fractional crystallization,
   wherein
   R represents an organic group that optionally contains one or more heteroatoms and that contains at least one carbon atom.

2. The process according to claim 1, wherein the zirconium compound has a melting point that is at least 3° C. higher than that of the hafnium compound.

3. The process according to claim 1, wherein the zirconium compound has a melting point that is at least 10° C. higher than that of the hafnium compound.

4. The process according to claim 1, wherein the crystallisation is performed between −70° C. and +100° C.

5. The process according to claim 3, wherein the crystallisation is performed between −20° C. and +70° C.

6. The process according to claim 1, wherein R represents identical or different groups $YR^1$ or $NR^2R^3$, in which
   Y represents O or S and
   $R^1$, $R^2$ and $R^3$ each, independently, represent a linear or branched, optionally substituted $C_1$-$C_{18}$-alkyl group, an optionally substituted $C_3$-$C_6$-cycloalkyl group or an optionally substituted $C_5$-$C_{24}$-aryl group.

7. The process according to claim 5, wherein R represents identical or different groups $YR^1$ or $NR^2R^3$, in which
   Y represents O or S and
   $R^1$, $R^2$ and $R^3$ each, independently, represent a linear or branched, optionally substituted $C_1$-$C_{18}$-alkyl group, an optionally substituted $C_3$-$C_6$-cycloalkyl group or an optionally substituted $C_5$-$C_{24}$-aryl group.

8. The process according to claim 1, wherein R represents identical $C_1$-$C_6$-oxyalkyl or di($C_1$-$C_6$-alkyl)amino groups.

9. The process according to claim 7, wherein R represents identical $C_1$-$C_6$-oxyalkyl or di($C_1$-$C_6$-alkyl)amino groups.

10. The process according to claim 1, wherein the mixture used for separation contains at most 10 wt. %, with respect to the total weight of the mixture, of an organic solvent that is inert towards the hafnium and zirconium compounds.

11. The process according to claim 9, wherein the mixture used for separation contains at most 10 wt. %, with respect to the total weight of the mixture, of an organic solvent that is inert towards the hafnium and zirconium compounds.

12. A process according to claim 1, wherein the fractional crystallization process is a melt crystallization process.

13. A process according to claim 11, wherein the fractional crystallization process is a melt crystallization process.

14. A process according to claim 1, wherein the mixture used for separation contains at most 3 wt. % of zirconium, with respect to the total weight of mixture.

15. A process according to claim 1, wherein the mixture used for separation contains at most 0.3 wt. %, of zirconium, with respect to the total weight of mixture.

16. A process according to claim 13, wherein the mixture used for separation contains at most 0.3 wt. %, of zirconium, with respect to the total weight of mixture.

17. A process according to claim 1, wherein the mixture used for separation contains at most 0.3 wt. % of zirconium, with respect to the total weight of mixture.

* * * * *